United States Patent [19]

Arichi et al.

[11] Patent Number: 4,524,067

[45] Date of Patent: Jun. 18, 1985

[54] SOYBEAN SAPONINS, AND A METHOD OF ISOLATING THE SAME

[75] Inventors: Shigeru Arichi; Yoshihiro Uchida, both of Osaka, Japan

[73] Assignee: Osaka Chemical Laboratory Co., Ltd., Osaka, Japan

[21] Appl. No.: 487,096

[22] Filed: Apr. 21, 1983

Related U.S. Application Data

[63] Continuation of Ser. No. 194,974, Oct. 8, 1980, abandoned.

[30] Foreign Application Priority Data

Oct. 29, 1979 [JP] Japan ................................ 54-140167
Nov. 20, 1979 [JP] Japan ................................ 54-150938
May 19, 1980 [JP] Japan ................................ 55-66284

[51] Int. Cl.$^3$ ...................... A61K 31/70; C07H 15/00; C07H 15/24
[52] U.S. Cl. ...................................... 514/33; 536/4.1; 536/5; 536/18.1

[58] Field of Search ................... 424/180, 182; 536/5, 536/6, 4.1, 18.1

[56] References Cited

U.S. PATENT DOCUMENTS

4,217,345 8/1980 Shinohara et al. .................. 424/180

OTHER PUBLICATIONS

Kitagawa et al., Chem. Pharm. Bull, vol. 21, pp. 121-129, 1976.

*Primary Examiner*—Blondel Hazel
*Attorney, Agent, or Firm*—Hubbell, Cohen, Stiefel & Gross

[57] ABSTRACT

This invention is directed to new saponins isolated from soybean seeds, a method for isolating the same and uses of the saponin component of soybeans as an antioxidant for foodstuffs or cosmetics and as an agent for affecting the metabolism in human beings.

2 Claims, No Drawings

SOYBEAN SAPONINS, AND A METHOD OF ISOLATING THE SAME

This is a continuation of application Ser. No. 194,974 filed Oct. 8, 1980 now abandoned for Soy Bean Saponins, and a method of isolating the same of Shigeru Arichi et al.

BACKGROUND OF THE INVENTION

1. Field of the Invention:

This invention relates to soybean saponins, their uses, and a method of isolating the same. More particularly, this invention is concerned with novel saponins separated from soybeans, metabolism affecting and antioxidizing compositions containing as an effective component a saponin which can be separated from soybeans, and a method of separating saponins from soybeans.

2. Description of the Prior Art:

It is known that various kinds of sapnonins occur in plants and animals, and that soybeans contain certain kinds of saponins, too. The soybean saponins are known to give by hydrolysis five kinds of sapogenols called soya sapogenols A, B, C, D and E, and three compounds giving soya sapogenol B, i.e., soya saponins I, II and III, are known by their chemical structures [see, for example, Chem. Pharm. Bull., 24(1), 121–129 (1978)]. It is known that these soya saponins are physiologically active in causing hemolysis, and killing fishes and insects [see I. E. Liener, "Toxic Constituents of Plant Foodstuffs", Academic Press, New York, 169 (1969)]; I. Ishaaya, Y. Birk, A. Bondi and Y. Tencer, J. Sci. Food Agr., 20,433 (1969) [C.A., 71, 89173 (1969)]; H. C. F. Su, R. D. Speirs and P. G. Mahany, J. Econ. Entomol., 65, 844 (1972) [C.A., 77, 84473 (1972)]; Y. Birk, A. Bondi, B. Gestetner and I. Ishaaya, "A Thermostable Hemolytic Factor in Soybeans", Nature, 197, 1089 (1963); or the like].

It is, however, believed that it is not known that saponins extracted from soybeans have a vital metabolic action, particularly for the inhibition of formation of lipid peroxides, and the promotion of metabolism of lipids and uric acid, and an antioxidizing action for food, or the like.

As is well known, the existence of lipid peroxides is very harmful to the human body. Serious attention has come to be paid to the relation between ageing and lipid peroxides, since J. Glavind et al. reported the existence of lipid peroxides in atherosclerotically hardened aortic lipids, and the presence of a mutual relationship between the degree of change in morbidity and the quantity of lipid peroxides [Acta Pathol. Microbiol. Scand., 30, 1 (1952)]. Aoyama et al. reported that arteriosclerosis would be caused by lipid peroxides [Jap. Heart J., 6, 128 (1965)]. Fukuzumi et al. reported that lipid peroxides had been found in the wall of the aorta in the chest of a man suffering from atherosclerosis, but that no lipid peroxide had been found in any normal aorta [Oil Chemistry, 10, 659 (1961); 12, 93 (1963); and 14, 119 (1965)]. Fukuzumi et al. also recognized the existence of conjugated diene hydroperoxides of fatty acids in cancerous tissues [Oil Chemistry, 10, 643 (1961); and 12, 165 (1963)]. Iizuka discussed the pathological significance of autoxidation in the formation of a cerebral tumor [Brains and Nerves, 14, 405 (1962)]. The toxic action of increased lipid peroxides on the living organisms was attributed, for example, to their relation to β-lipoproteins [Nishida et al., J. Lipid Res., 1, 450 (1960)], or the trouble which they might cause to the —SH groups in enzyme proteins [E. D. Wills, Biochem. Pharmacol., 7, 7 (1961)].

It is also known that lipid peroxides destroy various kinds of vitamins and cause trouble in the metabolism of fatty acids, leading to obesity. In the event lipid peroxides are formed by autoxidation of fatty acids, vitamin E (α-tocopherol) is known as an effective agent for inhibiting the formation of lipid peroxides to thereby prevent ageing. Vitamin E is, however, very expensive, and as it is insoluble in water and soluble in oil, it is stored in the body for a long period of time, and produces side effects. Vitamin $B_2$ (riboflavin) having no such disadvantage is, therefore, sometimes used, but disadvantageously has an extremely lower power of inhibiting the formation of lipid peroxides than vitamin E. It has, thus, been desired to develop a medicine which is inexpensive, soluble in water, safe to use, and has a high power of inhibiting the formation of lipid peroxides.

It is also well known that if oils and fats are left as they are, they are oxidized, and that the increased peroxides cause the so-called oil burning which lowers their flavor sharply. A variety of antioxidizing agents are usually employed for preserving food, cosmetics, or the like. Most of those antioxidizing agents are, however, chemically synthesized products, and it is not recommendable from the standpoint of safety to use them continuously for a long period of time. It has, therefore, been desired to develop a safer antioxidizing agent composed of a natural substance which can be derived from the food which one eats in his daily life.

SUMMARY OF THE INVENTION

According to this invention, there is provided a novel saponin which is separated from soybeans (Glycine max MERRILL), and which can be represented by the following structural formula:

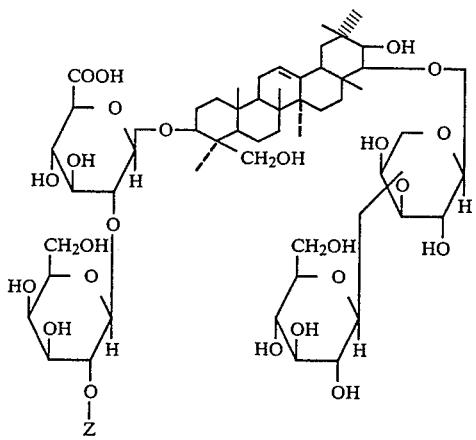

wherein Z stands for a hydrogen atom, or a D-glucopyranosyl group represented by the formula:

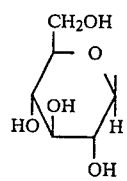

If Z stands for a hydrogen atom, the aforementioned formula represents a compound named 3-O-[β-D-galactopyranosyl-(1→2)-β-D-glucuronopyranosyl]-22-O-[β-D-glucopyranosyl (1→3)-α-L-arabinopyranosyl]-soyasapogenol A (hereinafter called soya-saponin $A_2$), and if Z stands for a D-glucopyranosyl group, the formula represents a compound named 3-O-[β-D-glucopyranosyl(1→2)-β-D-galactopyranosyl-(1→2)-β-D-glucuronopyranosyl]-22-O-[β-D-glucopyranosyl(1→3)-α-L-arabinopyranosyl]-soyasapogenol A (hereinafter called soyasaponin $A_1$). The invention also includes the non-toxic salts of those compounds, such as alkali metal or alkali earth metal salts thereof.

According to this invention, there is also provided a metabolism affecting composition comprising as an effective constituent a saponin component which can be separated from soybeans, and which contains at least the aforementioned novel saponin.

According to a further aspect of this invention, there is provided an antioxidizing composition comprising as an effective constituent a saponin component which can be separated from soybeans, and which contains at least the aforementioned novel saponin.

DETAILED DESCRIPTION OF THE INVENTION

The saponin component according to this invention can be obtained by extraction from soybeans, and purification with a solvent. The purification may also be carried out by using a resinous adsorbent for adsorbing the saponin selectively from the extract. The term "saponin component" as herein used means a mixture consisting substantially solely of the saponins obtained by the methods as herein described. Any of these soyasaponins is considered to occur in plants other than soybeans, too.

The saponin component can be obtained from soybeans by a number of methods, including those which will hereinafter be described.

Soybean seed powder is usually degreased with an ordinary fat-soluble organic solvent such as hexane, and its effective constituent is extracted with water, a lower aliphatic alcohol such as methanol, or a water-containing lower aliphatic alcohol, followed by evaporation of the extract to dryness. The extract is, then, dissolved in n-butanol saturated with water, and after water is added into the resulting solution, it is shaked, and left at rest, whereby the n-butanol layer is separated, followed by evaporation to dryness. Alternatively, the extract is dissolved in a mixed solution containing equal proportions of n-butanol and water, and the resulting solution is left at rest, whereby the n-butanol layer is separated, followed by evaporation to dryness. Then, the evaporation residue is dissolved in a lower aliphatic alcohol, and the resulting solution is injected into ether while it is being stirred. The precipitate is recovered by filtration to yield a saponin component.

According to another method, a powder of soybean seeds is degreased, and extracted with water, a lower aliphatic alcohol or a water-containing lower aliphatic alcohol. The concentrate thus obtained is dissolved in water, or water containing no more than about 30% of a lower aliphatic alcohol. The resulting solution is contacted with a porous, crosslinked resinous adsorbent having a macro-network structure (e.g., Cervachrome XAD), whereby a saponin component is adsorbed. The saponin is, then, desorbed from the adsorbent with a lower aliphatic alcohol, or water containing at least about 30% of a lower aliphatic alcohol.

The extract thus obtained consists substantially solely of the saponin component, and can be directly used as the effective constituent for this invention.

The saponin component according to this invention contains 0.5 to 0.7% by weight of a compound or compounds represented by formula I or II, which will hereinafter appear, based on the weight of the soybeans employed, or 0.7 to 1.0% by weight of any such compound based on the weight of the degreased soybeans, though the kind and quantity of any such compound may somewhat depend on the kind of the soybeans involved.

The soya-saponins have the following properties:
1. They are in the form of an odorless, slightly bitter powder having a yellowish white to brown color, and which is easily soluble in dilute methanol, soluble in water, methanol and ethanol, and hardly soluble in chloroform, ether, hexane and carbon tetrachloride.
2. The 1% aqueous solution thereof is neutral.
3. Infrared absorption:
   IR: γmax (nujol) 3,400 (br), 3,350 (br) and 1,720 (br) cm$^{-1}$;
   IR: γ(KBr) 3,400 (br), 3,350 (br), 2,918, 1,734 (br), 1,385 (br), 1,074 and 1,027 cm$^{-1}$.
4. Thin-layer chromatography:
   Support: A plate of kieselguhr 60 F 254 (Merck);
   Developing solvent: Chloroform/methanol/water (6:4:1).

Clear reddish violet saponin spots appear when a mixture of 1% ceric sulfate and 10% sulfuric acid is sprayed against the support under heat.
5. By acid hydrolysis, they produce glucuronic acid, galactose, glucose, arabinose, rhamnose and xylose from their water-soluble portion, and the main constitutive genins, i.e., soyasapogenol A ($C_{30}H_{50}O_4$) having a melting point of 310° C. to 312° C., and soyasapogenol B ($C_{30}H_{50}O_3$) having a melting point of 260° C. to 261° C. from their water-insoluble portion, with very small quantities of soyasapogenols C, D and E.
6. Their Liebermann and Salkowski reactions are both positive.
7. They form sustaining bubbles when shaked in water.

According to this invention, the saponin component coontains at least one of the soyasaponins represented by the following formulas I and II:

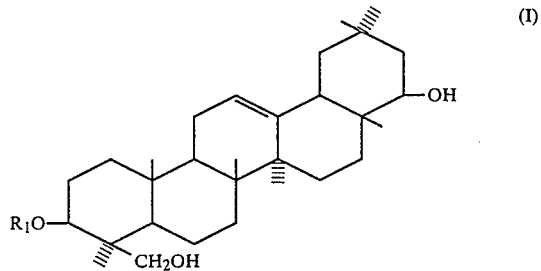
(I)

wherein $R_1$ stands for an α-L-rhamnopyranosyl-(1→2)-β-D-galactopyranosyl(1→2)-β-D-glucuronopyranosyl, α-L-rhamnopyranosyl (1→2)-α-L-arabinopyranosyl(1→2)-β-D-glycuronopyranosyl, or β-D-galactopyranosyl(1→2)-β-D-glucuronopyranosyl group;

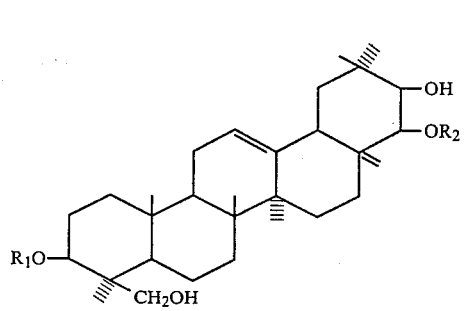

wherein $R_1$ stands for a β-D-glucopyranosyl-(1→2)-β-D-galactopyranosyl-(1→2)-β-D-glucuronopyranosyl group, and $R_2$ stands for a β-D-glucopyranosyl-(1→3)-α-L-arabinopyranosyl group, or $R_1$ stands for a β-D-galactopyranosyl-(1→2)-β-D-glucuronopyranosyl group, and $R_2$ stands for a β-D-glucopyranosyl(1→3)-α-L-arabinopyranosyl group.

The saponins of formulas I and II are those belonging to the oleanolic glycosides of triterpenes. Concrete names of the compounds represented by formula I include 3-O-[α-L-rhamnopyranosyl(1→2)-β-D-galactopyranosyl(1→2)-β-D-glucuronopyranosyl]-soyasapogenol B (soyasaponin I, $C_{48}H_{78}O_{18}\cdot 2H_2O$, having a melting point of 238° C. to 240° C.), 3-O-[α-L-rhamnopyranosyl(1→2)-α-L-arabinopyranosyl(1→2)-β-D-glucuronopyranosyl]-soyasapogenol B (soyasaponin II, $C_{47}H_{76}O_{17}\cdot 3H_2O$, having a melting point of 212° C. to 215° C.), and 3-O-[β-D-galactopyranosyl(1→2)-β-D-glucuronopyranosyl]-soyasapogenol B (soyasaponin III, $C_{48}H_{68}O_{14}\cdot 2H_2O$, having a melting point of 215° C. to 216° C.).

Concrete names of the compounds represented by formula II include 3-O-[β-D-glucopyranosyl(1→2)-β-D-galactopyranosyl(1→2)-β-D-glucuronopyranosyl]-22-O-[β-D-glucopyranosyl(1→3)-β-L-arabinopyranosyl]-soyasapogenol A (soyasaponin $A_1$), and 3-O-[β-D-galactopyranosyl(1→2)-β-D-glucuronopyranosyl]-22-O-[β-D-glucopyranosyl(1→3)-α-L-arabinopyranosyl]-soyasapogenol A (soyasaponin $A_2$).

These compounds may exist in the form of their non-toxic salts with alkali metals such as sodium and potassium, or alkali earth metals such as calcium and magnesium.

Soybeans contain a greater amount of soyasaponin I than any other saponin mentioned above. In addition to the saponins having the structures represented by formulas I and II, soybeans contain very small quantities of saponins having unknown structures, but of which the skeletons are formed by the following soyasapogenols C, D and E. These compounds also fall within the scope of the saponin component according to this invention.

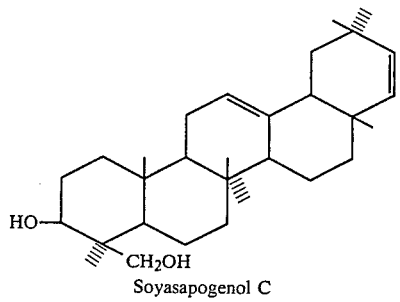
Soyasapogenol C

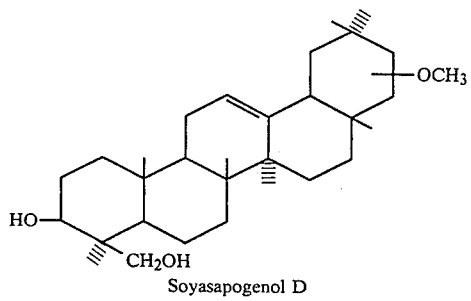
Soyasapogenol D

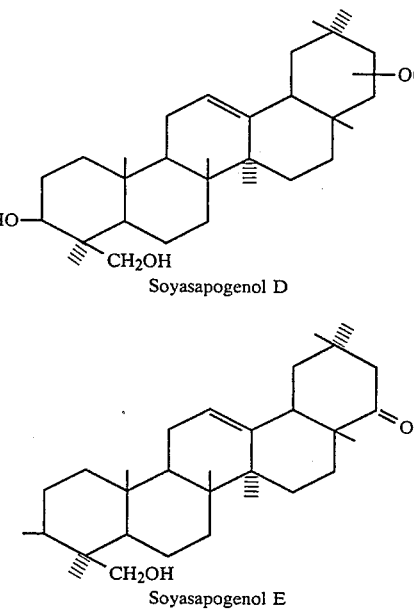
Soyasapogenol E

In order to obtain the individual compounds, the saponin component (i.e., a mixture of all the soyasaponins) obtained as hereinabove described may be separated by, for example, an appropriate combination of silica gel column chromatography, centrifugal liquid chromatography and high pressure liquid chromatography, using e.g. a developing solvent composed of a mixture of chloroform, methanol and water (i.e., a sublayer of the mixture having a chloroform/methanol/water ratio of 65:35:10) or a mixture of n-butanol, acetic acid and water. Alternatively, the n-butanol layer which is obtained by the treatment of the saponin component with water saturated n-butanol or a mixed solution of n-butanol and water (1:1), is further treated with a mixed solution of n-butanol and water (1:2), and its water transfer area is subjected to silica gel column chromatography. Then, it is desalted with an ion exchange resin such as Dowex 50 WX 8, whereby the individual compounds, particularly soyasaponins $A_1$ and $A_2$, are obtained. It is, however, more desirable from the economical standpoint to use a mixture of saponins than to separate it into the individual compounds.

The metabolism affecting composition according to this invention comprises a saponin component of soybean, and a pharmaceutically acceptable carrier. The composition may be prepared for either oral or parenteral administration.

Examples of the dosage form which can usually be employed for oral administration include powder, tablets, emulsions, capsules, teas, granules, and solutions, including tinctures, fluid extracts, spirits, suspensions, lemonades and syrups. Examples of the dosage form for parenteral administration include injections, drops, ointments, plaster, solutions (including spirits, tinctures and lotions), fomentation (poultice and paste), paints, aerosols, conspergatives, liniment (inunction), creams, emulsions, and bath.

A preparation for oral administration, an injection or a drop is effective if it is given to an adult two or three times a day so that he may take a daily total of 20 to 1,000 mg, preferably 30 to 200 mg, of the saponin component, though it may depend on the degree of his sickness. A preparation for parenteral and external use may contain 0.01 to 5%, preferably 0.1 to 1%, of the saponin component. It is desirable to prepare any composition in any dosage form so that it may contain the compound of this invention in the quantity required for each dose as will hereinafter be set forth in further detail.

It is possible to use any known solid or liquid excipient. Examples of the excipients used for preparing powders for oral administration include lactose, starch, dextrin, calcium phosphate, calcium carbonate, natural and synthetic aluminum silicate, magnesium oxide, dry aluminum hydroxide, magnesium stearate, sodium bicarbonate, and dry yeast.

Examples of the excipients for preparing powders for external use include zinc oxide, talc, starch, kaolin, boric acid, zinc stearate, magnesium stearate, magnesium carbonate, precipitated calcium carbonate, bismuth subgallate, and potassium aluminum sulfate. Liquid preparations may be made by using excipients, such as water, glycerin, propylene glycol, simple syrup, ethanol, fatty oils, ethylene glycol, polyethylene glycol and sorbitol. Ointments may be prepared by using excipients, such as fats, fatty oils, lanolin, vaselin, glycerin, yellow wax, Japan wax, paraffin, liquid paraffin, resins, higher alcohols, plastics, glycols and water surface active agents, which are combined to form hydrophobic or hydrophilic bases, including emulsion, water soluble and suspension bases.

Baths are preferably prepared by adding a diluent, such as sodium or potassium sulfate, to the saponin component of this invention.

The compositions according to this invention can be prepared in accordance with any procedure known in the art of manufacturing pharmaceutical preparations.

The saponin components of this invention inhibit the formation of lipid peroxides, and are effective for the prevention and treatment of arteriosclerosis, myocardosis, cerebral apoplexy, cerebral thrombosis, or the like, and the prevention of ageing. They are also useful for the prevention and treatment of gout by promoting the metabolism of uric acid, and for the prevention of obesity and the prevention and treatment of hyperlipemia by promoting the metabolism of lipids.

When the saponin component of this invention is used as an antioxidizing agent, it is usually used in its solid form, or in the form of a composition thereof. If it is mixed with an aqueous substance, it is used in its solid form or in the form of an aqueous solution thereof, but if it is mixed into an oily substance, it is used with a surface active agent such as Tween 80 (trade name of the product of Atlas Chemical Industry, U.S.A.), polyethylene glycol, glycerin, or the like, because the saponin component is hardly soluble in oils and fats. The saponin component is added in the quantity of at least 0.001% by weight and up to 2 or 3% by weight, in accordance with any customary procedure, together with other kinds of additives.

The saponin component of this invention, which is extracted from soybeans used for food, assures a very high degree of safety as evidenced by its $LD_{50}$ of at least 1 g/kg for mice when intraperitoneally injected. As opposed to most of the known antioxidizing agents which are hardly soluble in water, the saponin component of this invention is soluble in water, and has a high degree of thermal stability and a strong antioxidizing action. The antioxidizing agent composed of the saponin component according to this invention assures a very high degree of safety, and is, therefore, particularly suitable for use in applications involving direct relationship to the human body. More specifically, it is suitable for addition into foodstuffs such as edible oil, butter, cheese and other dairy products, ham, sausage and other meat products, canned foods, precooked foods, dried fish, and cakes and candies; soft and health drinks; cosmetics; or the like.

The saponin component of this invention will now be described with reference to examples of manufacture.

EXAMPLE OF MANUFACTURE 1

10 kg of powder of soybean seeds which were decreased with 100 liters of n-hexane twice for one hour each time under heating, were extracted with 100 liters of 99% methanol under heating twice for three hours each. After the solvent was removed from the extracted solution by vacuum distillation, the residue was treated with 10 liters of water saturated n-butanol under stirring on a water bath three times for about one hour each. The resulting solution was washed three times with three liters of water saturated with n-butanol, whereby all the sugar and pigment contained in the solution were removed by migration into water, and the water saturated n-butanol layer thus separated was subjected to vacuum distillation at a temperature not higher than 80° C. to dryness. The distillation residue was dissolved in three liters of methanol, and the resulting solution was injected into 60 liters of ether under stirring. After the solution was left to stand for one day, the precipitate was collected by filtration, and dried under reduced pressure at a temperature not higher than 60° C., whereby 30 g of a saponin component were obtained.

EXAMPLE OF MANUFACTURE 2

10 kg of powder of soybean seeds were degreased by extraction under heat with 100 liters of n-hexane twice for one hour each. The dry degreased product was extracted with 10 liters of 99% methanol at 60° C. for one hour. These procedures were repeated three times, and the resulting filtrates were combined, and dried by vacuum concentration at a temperature not higher than 60° C. The residue was dissolved in 100 ml of water, and the resulting solution was fed into the top of a column having an inside diameter of 8 cm, and filled with a dispersion in three liters of water of 1.8 kg of a synthetic resin adsorbent known under the name of Cervachrome XAD Type 2, and was caused to pass therethrough at a rate of 20 ml per minute, whereby saponin was adsorbed. Additional water was caused to flow down through the column continuously until the color of the effluent disappeared, whereby the impurities were removed. After the color of the effluent had disappeared, 99% methanol was caused to flow down through the column at a rate of 10 ml per minute, whereby the saponin was desorbed from the adsorbent. The completion of the desorption was checked by thin-layer chromatography using a support of kieselguhr F 254, and a mixed solvent composed of chloroform, methanol and water (65:35:10, sublayer). The detection was carried out by spraying a mixture of 1% ceric sulfate and 10% sulfuric acid, and heating at 105° C. for five minutes. The saponin was completely eluted with five liters of 99% methanol to flow down through the column. The elution thus obtained was evaporated at a temperature not higher than 60° C. to dryness, and the residue was dried at 60° C., whereby 32 g of a yellowish and brownish white saponin component were obtained.

EXAMPLE OF MANUFACTURE 3

10 kg of powder of soybean seeds were degreased by extraction twice under heat with 100 liters of n-hexane. The degreased powder was extracted with 100 liters of 98% methanol twice for three hours each, while it was being boiled. The resulting solution was subjected to vacuum distillation to yield 1.4 kg of an extract. This extract was dissolved in 100 liters of a mixture of n-butanol and water (1:1), and allowed to stand. The n-butanol layer was separated, and after the solvent was removed by vacuum distillation, the residue was dissolved in five liters of 98% methanol, and the resulting solution was added little by little into 100 liters of ethyl ether. The precipitate thus formed was separated by filtration, and 10 liters of water saturated n-butanol were added into the precipitate to separate it into the soluble and insoluble portions. The solvent was removed completely from the soluble portion by vacuum distillation to yield 64 g of a residue. This residue was distributed with 10 liters of a mixture of n-butanol and water (1:2). The aqueous layer was distilled under vacuum, and the resulting residue weighting 32 g was subjected to silica gel column chromatography using Merck's Silica Gel G having a particle size of 70 to 230 mesh, and an eluation solvent composed of chloroform, methanol and water (65:35:10 sublayer to 6:4:1). The eluate was, then, subjected to thin-layer chromatography using a support of Silica Gel 60 F 254, a developing solvent composed of chloroform, methanol and water (6:4:1), and a coloring agent composed of a mixed solution of 1% ceric sulfate and 10% sulfuric acid, whereby fractions containing soyasaponins $A_1$ and $A_2$ appearing at a flow rate $R_f$ of about 0.25 and about 0.30, respectively, were separated. After the solvent was removed from each fraction by vacuum distillation, the residue was suspended in 100 ml of water, and 1 g of a cation exchange resin known under the name of Dowex 50 WX 8 was added into the suspension, while it was being well stirred. The suspended matter was dissolved to transparency. Each aqueous solution obtained by filtration was evaporated to dryness under vacuum, whereby 1.9 g of soyasaponin $A_1$ and 1.2 g of soyasaponin $A_2$, which were both a white powder, were obtained. Each product was purified by recrystallization from aqueous methanol.

Soyasaponin $A_1$ has the following properties:

(1) It has a melting point of 240° C. to 242° C.

(2) It has a specific rotatory power of $[\alpha]_D^{26} +23.2°$ (C=0.9, methanol).

(3) Its infrared absorption spectrum (KBr) has a characteristic absorption maximum at 3,375 (broad and strong), 2,918, 1,737, 1,632, 1,385 (broad), 1,074 (broad and strong) and 1,027 (broad) cm$^{-1}$.

(4) It does not show any ultraviolet absorption at any wavelength greater than 210 nm.

(5) Its $^{13}$C-nuclear magnetic resonance spectrum (d$_5$-pyridine $\delta_c$) shows 172.1 (COOH), 144.0 (C$_{13}$), and 108.1, 106.5, 105.7, 104.5 and 102.9 (anomeric C).

(6) It is easily soluble in methanol, soluble in water, pyridine, dimethyl sulfoxide and ethanol, and insoluble in acetone, chloroform and ether.

(7) It is odorless, and its aqueous solution is weakly acidic (i.e., a solution obtained by dissolving 10 mg of soyasaponin $A_1$ in 1 ml of water has a pH value of 6).

(8) It is a colorless finely powdered crystal (as it is crystallized from aqueous methanol).

(9) It shows a flow rate $R_f$ of 0.25 when subjected to thin-layer chromatography using 0.25 mm precoated Silica Gel 60 F 254 of Merck, and a developing solvent composed of chloroform, methanol and water (6:4:1). It shows a bluish violet color when heated after a mixed solution of 1% ceric sulfate and 10% sulfuric acid is sprayed on the thin-layer chromatograph.

(10) When it is subjected to methanolysis (i.e., heated under reflux in 9% hydrochloric acid-dry methanol), it gives 1 mol each of methylgalactoside, methylarabinoside and methylglucuronide, and 2 mols of methylglucoside. A completely methylated compound ($C_{77}H_{132}O_{29}$) obtained by methylation of soyasaponin $A_1$ with methyl iodide, dimethyl sulfoxide and sodium hydride gives 1 mol each of methyl 3,4-di-O-methylglucopyranoside, methyl 3,4,6-tri-O-methylgalactopyranoside and methyl 2,4-di-O-methylarabinopyranoside, and 2 mols of methyl 2,3,4,6-tetra-O-methylglucopyranoside when subjected to methanolysis after reduction. It also gives 1 mol of 3,22,24-tri-O-methyl soyasapogenol A ($C_{33}H_{56}O_4$).

Soyasaponin $A_2$ has the following properties:

(1) It has a melting point of 231° C. to 233° C.

(2) It has a specific rotatory power of $[\alpha]_D^{21} +23.9°$ (C=0.9, methanol).

(3) Its infrared absorption spectrum (KBr) has a characteristic absorption maximum at 3,350 (broad and strong), 2,925, 1,740, 1,640, 1,385 (broad) and 1,027 (broad and strong) cm$^{-1}$.

(4) It does not show any ultraviolet absorption at any wavelength greater than 210 nm.

(5) Its $^{13}$C-nuclear magnetic resonance spectrum shows 172.2 (COOH), 144.0 (C$_{13}$), and 108.3, 106.0, 105.3 and 104.7 (anomeric C).

(6) It is easily soluble in methanol, soluble in water, pyridine, dimethyl sulfoxide and ethanol, and insoluble in acetone, chloroform and ether.

(7) It is odorless, and its aqueous solution is weakly acidic (i.e., a solution obtained by dissolving 5 mg of soyasaponin $A_2$ in 1 ml of water has a pH value of 6).

(8) It is a colorless fine crystal (as it is crystallized from aqueous methanol).

(9) It shows a flow rate $R_f$ of 0.3 when subjected to thin-layer chromatography using 0.25 mm precoated Silica Gel 60 F 254 of Merck, and a developing solvent composed of chloroform, methanol and water (6:4:1). It shows a bluish violet color when heated after a mixed solution of 1% ceric sulfate and 10% sulfuric acid is sprayed on the thin-layer chromatograph.

(10) When it is subjected to methanolysis, it gives 1 mol each of methylglucoside, methylgalactoside, methylarabinoside and methylglucuronide. A completely methylated compound ($C_{68}H_{116}O_{24}$) obtained by methylation of soyasaponin $A_2$ with methyl iodide, dimethyl sulfoxide and sodium hydride gives 1 mol each of methyl 3,4-di-O-methylglucopyranoside, methyl 2,4-di-O-methylarabinopyranoside, methyl 2,3,4,6-tetra-O- methylgalactopyranoside and methyl 2,3,4,6-tetra-O-methylglucopyranoside as methylated sugar, and 1 mol of 3,22,24-tri-O-methyl soyasapogenol A as methylated sapogenol, when subjected to methanolysis after reduction.

EXAMPLE OF MANUFACTURE 4

2 kg of powder of soybean seeds were degreased by extraction twice under heat with 20 liters of n-hexane. The dry degreased product was extracted under heat with 20 liters of 98% methanol twice for three hours each, while it was being boiled. The solution was subjected to vacuum distillation to yield 160 g of an extract. This extract was dissolved in 20 liters of a mixed solution of n-bitanol and water (1:1), and left to stand at rest. The n-butanol layer was separated, and after the solvent was removed by vacuum distillation, the residue weighing 50 g was dissolved in 1 liter of 98% methanol, and the resulting solution was added little by little into 20 liters of ethyl ether. The precipitate thus formed was collected by filtration (35 g), and subjected to column chromatography using Merck's Silica Gel G having a particle size of 70 to 230 mesh and an eluation solvent composed of chloroform, methanol and water (65:35:10 sublayer), followed by active carbon treatment, whereby 12 g of total soyasaponin were obtained. It was subjected to centrifugal liquid chromatography using KT gel at 500 rpm, whereby 2.52 g of soyasaponin I, 0.45 g of soyasaponin II, 0.21 g of soyasaponin III, 0.40 g of soyasaponin $A_1$ and 0.48 g of soyasaponin $A_2$ were separated as the individual compounds.

The following is a description of the results of the pharmacological tests conducted on the saponin component obtained according to Example 1 above.

PHARMACOLOGICAL TESTS FOR INHIBITION OF FORMATION OF LIPID PEROXIDES

It is widely known that Adreamycin, which is an oncostatic, inhibits the synthesis of DNA by combining therewith, and the metabolism of lipids in the heart to cause deposition of lipid peroxides therein, leading to miocardosis.

The inventors of this invention has compared the action for inhibiting the formation of lipid peroxides between the saponin component of this invention, and α-tocopherol (vitamin E) and riboflavin (vitamin $B_2$) known as agents for inhibiting the formation of lipid peroxides. They have found the saponins of this invention substantially comparable to vitamin E, and about twice more effective than vitamin $B_2$. The test results are as follows:

TEST METHOD (1) The tests were conducted with groups of five COF male mice, five week old, weighing 20 to 25 g each. 15 mg/kg of Adreamycin (product of Kyowa Hakko Kogyo, Japan) were intraperitoneally injected into each mouse (0.15 ml of the medicine per 10 g of mouse weight).

The administration of each of the medicines to be tested as shown in Table 1 below was started one day prior to the administration of Adreamycin, and continued intraperitoneally for five days at a rate of 0.10 ml per 10 g of mouse weight. All the medicines tested were suspended or emulsified (only vitamin E) in a 0.9% physiological solution of sodium chloride, or a 0.9% physiological solution of sodium chloride containing 1% of Tween 80 immediately before they were applied.

All the medicines tested were administered at noon every day, and Adreamycin was given three hours after the administration of the medicines tested. The saponin component of this invention was given in the amount of 1,000 mg/kg, 500 mg/kg, 125 mg/kg, 50 mg/kg, 25 mg/kg and 12.5 mg/kg, vitamin E in the amount of 1,000 mg/kg and 250 mg/kg, and vitamin $B_2$ in the amount of 1,000 mg/kg, while a 0.9% physiological solution of sodium chloride was given to the mice of the control group.

(2) On the sixth day, each mouse was killed by dislocation of the cervical vertebrae, and its heart and liver were picked out immediately. After their wet weights were measured, a 2% homogenate was prepared with a 0.9% physiological solution of sodium chloride by a Potter homogenizer made of Teflon while it was being cooled with ice. This homogenate was used for determining the quantities of the lipid peroxides in the heart and liver in accordance with the improved Yagi's method, followed by comparison with the results obtained on the control group.

0.5 ml of a 3% aqueous solution of sodium lauryl sulfate was added into 0.2 ml of the aforementioned 2% homogenate, and they were mixed together by shaking for 30 seconds. Then, 1.5 ml of an acetic acid buffer solution having a pH value of 3.6, and 1.5 ml of a 0.8% solution of thiobarbituric acid were added thereinto, followed by addition of distilled water to make a total of 4.0 ml. After the resulting solution was shaked vigorously for 30 seconds, it was heated at 95° C. for an hour in an oil bath, and cooled with flowing water for five minutes. Then, 1.0 ml of 0.2N hydrochloric acid and 5.0 ml of a mixed solution of n-butanol and pyridine (15:1) were added into the solution, and after it was shaked violently, it was subjected to centrifugal separation at 3,000 rpm for 15 minutes, whereby the top n-butanol layer was separated, and its fluorescence spectrum was measured by a spectrophotofluorometer (Ex 515 nm and Em 553 nm). These procedures had previously been repeated by using a malonaldehydic standard solution to form a working curve showing the relation between the fluorescence spectrum and the quantity of lipid peroxides. The quantity of lipid peroxides was obtained by applying the working curve to the values as actually measured.

[TEST RESULTS]

The rate of inhibition of the formation of lipid peroxides was obtained in accordance with the following equation to compare the effects of the various medicines tested, and the quantities thereof employed, as shown in Table 1:

$$\text{Rate of inhibition (\%)} = \frac{C - D}{C - A} \times 100$$

wherein
A: the concentration of lipid peroxides in the group of mice to which no Adreamycin had been given;
C: the concentration of lipid peroxides in the control group to which Adreamycin had been given; and
D: the concentration of lipid peroxides in the groups of mice to which both Adreamycin and the medicines to be tested had been administered.

Note: The rate of inhibition by each dosage was calculated by comparison with the values shown for the respective test numbers in the control group (i.e., applying the values of C shown for the control group).

It is obvious from the results shown in Table 1 that while the administration of Adreamycin increases the lipid peroxides in the heart and liver, the use of the saponin component according to this invention largely inhibits the formation of lipid peroxides. More specifically, the use of 125 to 250 mg/kg of the saponin component completely inhibited the formation of lipid peroxides in the heart, and the saponin component also showed a rate of inhibition of at least 80% against the formation of lipid peroxides in the liver. It was found substantially comparable to vitamin E ($\alpha$-tocopherol) which had been considered as a very effective agent for inhibiting the formation of lipid peroxides, and about twice more effective than vitamin $B_2$ (riboflavin).

The effectiveness of the saponin component according to this invention will now be described with reference to clinical cases.

mg/dl; lipid 960 U/liter; erythrocyte count $460 \times 10^4/mm^3$; leukocyte count $7.4 \times 10^3/mm^3$; urine+for protein and glucose.

The patient took a tablet containing 50 mg of the saponin component according to this invention each after breakfast and dinner every day for about 1.5 months continuously until October 12. As the result, she became able to sleep well at night, as she no longer had any stiffness in her shoulders, nor did she feel languid in her body any more. She ceased to suffer from any appreciable headache, and her dizziness was improved. She, however, still has ringing ears.

At the time of her first examination, she measured 121 cm around the abdomen and 103 cm around the chest, and weighed 74 kg, but her abdomen circumference has been reduced to 101 cm, her chest circumference to 94 cm, and her weight to 71 kg. Her abdominal wall has

TABLE 1

|   | Medicine | Test No. | Heart (n = 5) Lipid peroxide (nmol/g) | Rate of inhibition | Liver (n = 5) Lipid peroxide (nmol/g) | Rate of inhibition |
|---|---|---|---|---|---|---|
| C | 0.9% physiological sodium | I | 199.23 ± 30.46 | 0 | 138.69 ± 35.03 | 0 |
|   | chloride solution | II | 142.60 ± 7.77 | 0 | 136.58 ± 7.88 | 0 |
|   | (control) | III | 137.62 ± 9.75 | 0 | 151.33 ± 31.00 | 0 |
| D | Saponin component |  |  |  |  |  |
|   | (1000 mg/kg) | I | 114.40 ± 18.25 | 75.88 | 103.66 ± 8.63 | 53.83 |
|   | (500 mg/kg) | II | 92.16 ± 18.31 | 91.43 | 96.53 ± 13.40 | 63.61 |
|   | (250 mg/kg) | II | 82.37 ± 15.65 | 109.17 | 84.37 ± 13.05 | 82.93 |
|   | (125 mg/kg) | II | 85.86 ± 11.03 | 102.85 | 85.47 ± 18.63 | 81.18 |
|   | (50 mg/kg) | III | 111.81 ± 7.32 | 51.42 | 106.14 ± 14.98 | 58.15 |
|   | (25 mg/kg) | III | 132.06 ± 12.67 | 11.08 | 132.90 ± 8.68 | 23.72 |
|   | (12.5 mg/kg) | III | 130.14 ± 11.01 | 14.90 | 129.49 ± 16.89 | 28.10 |
|   | Vitamin E |  |  |  |  |  |
|   | (1000 mg/kg) | I | 106.87 ± 36.40 | 82.61 | 89.27 ± 26.33 | 75.95 |
|   | (250 mg/kg) | II | 86.34 ± 12.61 | 101.98 | 76.90 ± 8.15 | 94.79 |
|   | Vitamin $B_2$ (1000 mg/kg) | I | 153.61 ± 11.12 | 40.81 | 124.84 ± 10.26 | 21.28 |
| A | No medicine used |  | 87.43 ± 7.12 | — | 73.62 ± 4.23 | — |

CLINICAL CASE 1

H. Y., 54-year-old housewife.
First Examination: Aug. 26, 1979.
Name of Disease: Hyperlipemia, and arteriosclerosis.
Family History: Her father died of cerebral apoplexy when he was 61 years old, and her mother died of a heart disease when she was 57 years old.
Past History: She suffered from high blood pressure, and received treatment twelve years ago.
Present Sickness: She has been suffering from headache and ringing of her ears since three years ago, and has suffered from stiffness in her shoulders and dizziness of late, resulting in insomnia. She consulted a doctor in her neighborhood, and he diagnosed her case as arteriosclerosis and high blood pressure. She has received various kinds of medical treatment, but not recovered to date.
History of Treatment: At the time of her first examination, she was well-built, overnourished and obese, had a fair, but delicate skin, and was allergic. Her heart was enlarged on both sides, and cardiac murmurs were heard. Her pulse was tense and rapid, and her blood pressure was 160 systolic and 96 diastolic. Her liver was enlarged two fingerbreadths, and there was a pain on pressure on both sides of her abdomen. The results of biochemical examination and blood analysis were as follows:

Glucose 83 mg/dl; cholesterol 260 mg/dl; neutral fat 274 mg/dl; total protein 7.2 g/dl; albumin 4.3 g/dl; GOT 24 U/liter; GPT 20 U/liter; BUN 15 mg/dl; creatinine 0.9 mg/dl; uric acid 2.4 mg/dl; $\beta$-lipoprotein 820 become soft, the fatty deposits have been sharply reduced, and the tenderness on both sides of the abdomen has disappeared. Other symptoms have been improved as compared with those found at the time of her first examination.

The results of biochemical examination and blood analysis have also shown an improvement, especially in the amounts of cholesterol and fat in the blood, and the urine test for protein and glucose, as follows:

Glucose 83 mg/dl; cholesterol 192 mg/dl; neutral fat 117 mg/dl; total protein 7.0 g/dl; albumin 4.4 g/dl; GOT 31 U/liter; GPT 26 U/liter; BUN 17 mg/dl; creatinine 0.9 mg/dl; uric acid 2.4 mg/dl; $\beta$-lipoprotein 456 mg/dl; lipid 592 U/liter; erythrocyte count $464 \times 10^4/mm^3$; leukocyte count $5.7 \times 10^3/mm^3$; urine—for protein and glucose.

As is obvious from these figures, the amounts of the lipid in the blood, and the fatty deposits in her body have been reduced, and the various symptoms of her disease have been improved accordingly.

CLINICAL CASE 2

K. O., 43-year-old man, company employee.
First Examination: Oct. 3, 1979.
Name of Disease: Hyperlipemia and high blood pressure.
Family History: His father died of myocardial infarction when he was 57 years old, and his 77-year-old mother has been suffering from high blood pressure.
Past History: He suffered from gout three years ago.

Present Sickness: He has been suffering from severe stiffness in his shoulders since two years ago, and palpitation sometimes. He has recently come to be easily surprised, and cannot sleep at night. His case was diagnosed as high blood pressure and hyperlipemia, and he has received treatment in vein.

History of Treatment: At the time of his first examination, he was well-built and slightly obese, and has a dark complexion. His pulse was tense, but his pulse rate was normal. His heart was slightly enlarged, but no enlargement was found in his liver. His abdominal wall was hard, and slightly swollen. An electrocardiogram showed cardiac enlargement.

The biochemical examination and blood analysis gave the following results:

Glucose 116 mg/dl; cholesterol 292 mg/dl; neutral fat 244 mg/dl; total protein 7.0 g/dl; albumin 4.4 g/dl; GOT 34 U/liter; GPT 32 U/liter; creatinine 0.8 mg/dl; BUN 18 mg/dl; uric acid 7.4 mg/dl; $\beta$-lipoprotein 834 mg/dl; lipid 1,107 U/liter; urine—for protein and glucose; erythrocyte count $463 \times 10^4/mm^3$; leukocyte count $4.6 \times 10^3/mm^3$.

A tablet containing 50 mg of the saponin component according to this invention was administered to the patient each after breakfast and dinner every day for about one month continuously from October 3 to November 5. As the result, he became able to sleep well, and the stiffness in his shoulders was completely removed, though he still had a headache sometimes. His blood pressure was reduced from 171/98 at the time of his first examination to 144/91. His abdominal wall was softened. His abdominal girth was reduced from 110 cm at the time of the first examination to 92 cm, his chest circumference from 103 cm to 97 cm, and his weight from 77 kg to 74 kg. The results of the biochemical and blood analysis were improved, as follows:

Glucose 77 mg/dl; cholesterol 205 mg/dl; neutral fat 156 mg/dl; total protein 7.4 g/dl; albumin 4.9 g/dl; GOT 21 U/liter; GPT 34 U/liter; BUN 12 mg/dl; creatinine 0.8 mg/dl; uric acid 7.4 mg/dl; $\beta$-lipoprotein 403 mg/dl; lipid 547 U/liter; urine—for protein and glucose; erythrocyte count $460 \times 10^4/mm^3$; and leukocyte count $4.6 \times 10^3/mm^3$.

As is obvious from these figures, the amount of the lipid in the blood was reduded to the normal level, the fatty deposits in the body have been decreased, and the blood pressure was lowered, resulting in a greatly improved physical condition of the patient.

CLINICAL CASE 3

S. Y., 47-year-old man, governmental office employee.

First Examination: Oct. 5, 1979.

Name of Disease: Gout and hyperlipemia.

Family History: There is nothing is particular to be mentioned.

Past History: There is nothing to be mentioned.

Present Sickness: He was for the first time attacked by gout three years ago, and has since been suffering from gout two or three times a year when he ate meat. The doctor has recently pointed out that his blood contains a lot of neutral fat. He often suffers from stiffness in his shoulders, and sometimes has a headache. His right foot was attacked by gout one month ago, and he still feels a slight pain on pressure. He has consulted a doctor in his neighbourhood, and received his treatment entirely in vein.

History of Treatment: At the time of his first examination, he was well-built and slightly obese, and had a red face and a slightly dark skin. His pulse was large, strong and slightly rapid. An X-ray study of his chest indicated enlargement of the heart on both sides, and the point test showed a poor result. An electrocardiogram indicated the same results, and showed a low voltage. The results of blood analysis were as follows:

Glucose 99 mg/dl; cholesterol 270 mg/dl; neutral fat 262 mg/dl; total protein 7.1 g/dl; albumin 4.6 g/dl; GOT 30 U/dl; GPT 33 U/dl; BUN 19 mg/dl; creatinine 1.2 mg/dl; uric acid 9.2 mg/dl; $\beta$-lipoprotein 1,124 mg/dl; lipid 834 U/liter; erythrocyte count $462 \times 10^4/mm^3$; leukocyte count $7.6 \times 10^{-3}/mm^3$; urine—for protein and glucose.

A tablet containing 50 mg of the saponin component according to this invention was given to the patient after each of the three meals every day continuously for about one month from October 5 to November 10. As the result, all of his subjective symptoms disappeared, and his health was substantially restored. His weight was reduced from 72 kg to 70 kg, his chest circumference from 94 cm to 86 cm, and his abdominal girth from 103 cm to 87 cm, owing to a sharp reduction of the fatty deposits. The blood analysis also showed the following improvement:

Glucose 72 mg/dl; cholesterol 184 mg/dl; neutral fat 152 mg/dl; total protein 7.2 g/dl; albumin 5.2 g/dl; GOT 21 U/dl; GPT 19 U/dl; BUN 16 mg/dl; creatinine 1.2 mg/dl; uric acid 4.9 mg/dl; $\beta$-lipoprotein 443 mg/dl; lipid 594 U/liter; erythrocyte count $460 \times 10^4/mm^3$; leukocyte count $7.6 \times 10^{-3}/mm^3$; urine—for protein and glucose.

These results indicate a sharp reduction of uric acid to the normal level, a reduction of cholesterol, neutral fat and $\beta$-lipoprotein to their respective normal levels, and a decrease of lipid to nearly its normal level. The fatty deposits in the tissues of his body showed a reduction, too, leading to a remarkable improvement of his gout and hyperlipemia.

EXAMPLES OF PHARMACEUTICAL COMPOSITIONS

1. Gelatinous capsules (globular shape of inner diameter of 0.8 cm), containing in its five capsule:

| Wheat germ oil | 980 mg |
| Spirulina | 200 mg |
| The saponin component | 20 mg |

2. A tablet prepared by the following composition:

| The saponin component | 25 mg |
| Lactose | 75 mg |

3. A tablet prepared by the following composition:

| The saponin component | 50 mg |
| Lactose | 100 mg |

4. Granules prepared by the following composition:

| The saponin component | 100 mg |
| Lactose | 4.4 g |

ANTIOXIDIZING TEST

Attention is now directed to the results of the tests conducted for ascertaining the antioxidizing action of the saponin component obtained in Example 1 above.

1. Antioxidizing Action for Linoleic Acid and Frying Oil.

(1) Substances used for the Tests:
   Linoleic acid: Product of Wako Junyaku, Japan;
   Frying oil: Soybean oil made by Honen Seiyu Co., Ltd., Japan.

(2) Test Method:

A mixture containing 10 g of linoleic acid, 8% by weight of Tween 80 and 1% by weight of the saponin component was placed in a bath having a controlled temperature of 60° C., and aerated continuously by an air pump. A sample was picked up every hour until the lapse of three hours, and its peroxide value was determined in accordance with a customary procedure (The Japanese Society of Pharmacy, "Methods of Sanitary Tests for Frequent Use, and Explanatory Notes Therefor", 6th edition, pages 61 and 62, 1976, Nanzando, Japan).

A mixture containing 50 g of frying oil, 14% by weight of Tween 80 and 1% by weight of the saponin component was placed in a bath of boiling water, and aerated continuously by an air pump. A sample was picked up every three hours until the lapse of 18 hours, and its peroxide value was determined.

A control test solution containing no saponin component was prepared with each of linoleic acid and frying oil.

Tables 2 and 3 show the results of the tests involving linoleic acid and frying oil, respectively.

TABLE 2

Antioxidizing action for linoleic acid. (peroxide value in meq./kg)

| Test No. | Specimen | 0 | 1 | 2 | 3 | Rate of inhibition of increase in peroxide value after 3 hrs. (%)* |
|---|---|---|---|---|---|---|
| 1 | Control | 12 | 118 | 341 | 467 | 0 |
|   | Linoleic acid Containing Saponin | 12 | 42 | 113 | 228 | 52.5 |
| 2 | Control | 15 | 117 | 337 | 465 | 0 |
|   | Linoleic acid Containing Saponin | 15 | 39 | 96 | 199 | 59.1 |
| 3 | Control | 16 | 122 | 286 | 500 | 0 |
|   | Linoleic acid Containing Saponin | 16 | 43 | 111 | 251 | 51.4 |

TABLE 3

Antioxidizing action for frying oil. (peroxide value in meq./kg)

| | 0 | 3 | 6 | 9 | 12 | 15 | 18 | Rate of inhibition of increase in peroxide value after 18 hr (%)* |
|---|---|---|---|---|---|---|---|---|
| Control | 4 | 14 | 32 | 48 | 70 | 99 | 125 | 0 |
| Frying oil containing saponin | 4 | 5 | 6 | 10 | 17 | 26 | 38 | 71.9 |

Note:
*Rate of inhibition of increase in peroxide value after X hours
$= \frac{A - B}{A} \times 100$ wherein A: peroxide value of control (value measured after X hours − value after 0 hour); and
B: peroxide value of linoleic acid or frying oil (value measured after X hours − value after 0 hour).

(3) Test Results:

When linoleic acid was maintained at 60° C. and aerated for three hours, its peroxide value was in the range of 467 to 500 meq./kg, but if it contained 1% by weight of the saponin component according to this invention, its peroxide value was reduced to a range of 199 to 251 meq./kg. Thus, the rate of inhibition by the saponin component against an increase of the peroxide value was 54.3% on an average. When frying oil was maintained at 100° C. and aerated for 18 hours, its peroxide value was 125 meq./kg, but if it contained 1% by weight of the saponin component, its peroxide value was reduced to 38 meq./kg. Thus, the saponin showed a rate of 71.9% for inhibiting an increase of the peroxide value. It is, therefore, obvious that the saponin component of this invention exhibits an excellent antioxidizing action at a considerably high temperature.

2. Antioxidizing Action for Salad Oil.

(1) Substance Used for the Test:
   Salad oil: Product of Nisshin Seiyu Co., Ltd., Japan.

(2) Test Method:

Test oils were prepared by using various kinds of saponin components which were added into the salad oil in the amounts of 1 mg/ml and 0.1 mg/ml. These test oils and a control oil containing no saponin component were heated at 180° C. for 40 minutes, while oxygen was being blown thereinto. After they were cooled, the quantities of the lipid peroxides formed in the oils were determined by the Yagi's method [K. Yagi, Biochemie. Med., 15, 212 (1976); and K. Yagi, Vitamins, 49, 403 (1975)]. The results are shown in Table 4 below.

TABLE 4

| | Quantity of lipid peroxide (nmol/ml) | Rate of inhibition of increase in lipid peroxide (%)** |
|---|---|---|
| Salad oil not heated | 9.4 | — |
| Salad oil heated at 180° C. for 40 min. (Control) | 61.3 | — |
| Salad oil containing saponin component, and heated as above | | |
| Quantity of saponin Component added | | |
| Soyasoponin I (1 mg/ml) | 10.6 | 97.7 |
| Soyasoponin I (0.1 mg/ml) | 45.6 | 30.3 |
| Soyasoponin II (1 mg/ml) | 80.6 | −37.2 |
| Soyasoponin II (0.1 mg/ml) | 46.3 | 28.9 |
| Soyasoponin III (1 mg/ml) | 8.8 | 101.2 |
| Soyasoponin III (0.1 mg/ml) | 45.6 | 30.3 |
| Soyasoponin $A_1$ (1 mg/ml) | 13.8 | 91.5 |
| Soyasoponin $A_1$ (0.1 mg/ml) | 22.5 | 74.8 |
| Soyasoponin $A_2$ (1 mg/ml) | 38.8 | 43.4 |

TABLE 4-continued

|  | Quantity of lipid peroxide (nmol/ml) | Rate of inhibition of increase in lipid peroxide (%)** |
|---|---|---|
| Soyasoponin A$_2$ (0.1 mg/ml) | 60.0 | 2.5 |

Note:

**Rate of inhibition of increase in lipid peroxide (%) = $\frac{A - B}{A} \times 100$ wherein A: Quantity of lipid peroxide in control − quantity of lipid peroxide in salad oil not heated; and
B: Quantity of lipid peroxide in salad oil containing the saponin component − quantity of lipid peroxide in salad oil not heated.

(3) Test Results:

While the various kinds of saponin components employed showed different degrees of antioxidizing action, the use of 1 mg/ml of soyasaponin I exhibited as high a rate as 97.7% for inhibiting an increase of lipid peroxides in the salad oil.

3. Antioxidizing Action for Dried Fish.

A saurel had its abdomen cut for removal of its internal organs, and the quantity of lipid peroxides in the fish was determined by the Yagi's method after its tail portion occupying ¼ of its total length was cut away. The rest of the fish was longitudinally cut into two halves. One half of the fish was immersed in a 1% by weight aqueous solution of the saponin component for half an hour, while the other half was left as it was. Both of the halves were dried by direct exposure to the sun, and the quantities of lipid peroxides were determined for both of them by the Yagi's method. The results were as follows:

| | |
|---|---|
| Quantity of lipid peroxides in the tail portion: | 52 ± 4 n mol/g |
| Quantity of lipid peroxides in the half of the fish immersed in a 10% by weight aqueous solution of the saponin component, and dried | 225 ± 6 n mol/g |
| Quantity of lipid peroxides in the other half of the fish dried without being immersed in the saponin solution | 1,887 ± 44 n mol/g |

As is obvious from these results, the immersion of fish in the aqueous solution of the saponin component according to this invention contributed to a sharp reduction in the quantity of lipid peroxides formed therein.

What we claim is:

1. Substantially pure 3-0-[β-D-glucopyranosyl-(1→2)-β-D-galactopyranosyl-(1→2)β-D-glucuronopyranosyl]-22-0-[β-D-glucopyranosyl-(1→3)-β-L-arabinopyranosyl]-soyasapogenol A (-soyasaponin A$_1$) or substantially pure 3-0-[β-D-galactopyranosyl-(1→2)-β-D-glucuronopyranosyl]-22-0-[β-D-glucopyranosyl-(1→3)-α-L-arabinopyranosyl]-soyasapogenol A (soyasaponin A$_2$), or non-toxic salt thereof.

2. A composition having antioxidizing and metabolism affecting activity comprising an effective amount of either soyasaponin A$_1$ or soyasaponin A$_2$ and a carrier.

* * * * *